US008452408B1

(12) United States Patent
Song et al.

(10) Patent No.: US 8,452,408 B1
(45) Date of Patent: May 28, 2013

(54) PROMOTION OF BRAIN SELF-REPAIR MECHANISMS BY STEREOTAXIC MICRO-STIMULATION

(75) Inventors: Shijie Song, Tampa, FL (US); Juan Sanchez-Ramos, Tampa, FL (US)

(73) Assignees: University of South Florida, Tampa, FL (US); Department of Veterans Affairs, Washington, DC (US)

( * ) Notice: Subject to any disclaimer, the term of this patent is extended or adjusted under 35 U.S.C. 154(b) by 529 days.

(21) Appl. No.: 12/491,893

(22) Filed: Jun. 25, 2009

Related U.S. Application Data

(60) Provisional application No. 61/075,586, filed on Jun. 25, 2008.

(51) Int. Cl.
  *A61N 1/36* (2006.01)
(52) U.S. Cl.
  USPC .............................................. 607/45; 128/907
(58) Field of Classification Search
  USPC .............................................. 607/45; 128/907
  See application file for complete search history.

(56) References Cited

U.S. PATENT DOCUMENTS

| | | | |
|---|---|---|---|
| 4,114,606 A * | 9/1978 | Seylar | 600/409 |
| 6,528,245 B2 | 3/2003 | Sanchez-Ramos et al. | |
| 2002/0055530 A1 * | 5/2002 | Neuberger et al. | 514/381 |
| 2003/0139410 A1 | 7/2003 | Sugaya et al. | |
| 2004/0049121 A1 * | 3/2004 | Yaron | 600/544 |
| 2005/0169896 A1 | 8/2005 | Li et al. | |
| 2006/0251616 A1 | 11/2006 | Kollet et al. | |
| 2007/0067001 A1 * | 3/2007 | Lozano et al. | 607/42 |

OTHER PUBLICATIONS

Growth inhibitory factor (GIF) can protect from brain damage due to stab wounds in rate brain; Hozum et al; Neuroscience Letters 395 (2006) 220-223.*
Neurogenesis in Tα-1 tubulin transgenic mice during development and after injury; Coksaygan et al. Experimental Neurology 197 (2006) 475-485.*
Temporally Specific Proliferation Events Are Induced in the Hippocampus Following Acute Focal Injury, Carl Ernst and Brian R. Christie, Journal of Neurosciece Research 83:349-361 (2006).*
The glial scar and central nervous system repair, to James W. Fawcett and Richard A. Asher published in Brain Research bulletin, vol. 49, No. 6, pp. 377-391, 1999.*
Evidence That Nucleocytoplasmic Olig2 Translocation Mediates Brain-Injury-Induced Differentaion of Glial Precursors to Astrocytes to Mattson et al; Journal of Neuroscience Research 85:2126-2137 (2007).*

(Continued)

*Primary Examiner* — Carl H Layno
*Assistant Examiner* — Paula J Stice
(74) *Attorney, Agent, or Firm* — Michele L. Lawson; Smith & Hopen, P.A.

(57) ABSTRACT

A method of treating neurological deficit in which the brain area affected is focally and precisely stimulated by the transient insertion and subsequent removal of a micro-needle. This insertion and subsequent removal of the micro-needle induces endogenous stem cells to proliferate, migrate and promote the brain's self-repair mechanisms. The micro-needle stimulation causes the birth of new neural cells within the brain as well as mobilizes bone marrow derived cells with a neuronal phenotype to migrate to the site of stimulation to repair and replace damaged neural cells. By repairing and/or replacing injured or dead cells, this approach will slow down the degenerative course of the disease and may result in reversal of symptoms.

18 Claims, 6 Drawing Sheets

OTHER PUBLICATIONS

Neuronal cell loss accompanies the brain tissue response to chronically implanted silicone microelectrode arrays to Tresco et al in Experimental Neurology 195 (2005) 115-126.*

Alvarez-Buylla, et al., Birth, Migration, Incorporation, and Death of Vocal Control Neurons in Adult Songbirds, Neurobiology, 1997, vol. 33, pp. 585-601.

Song, et al., Preparation of Neural Precursors from Bone Marrow, Methods in Molecular Biology, 2002, vol. 198, pp. 79-86.

Friedenstein, et al., The Development of Fibroblast Colonies in Monolayer Cultures of Guinea-Pig Bone Marrow and Spleen Cells, Cell Tissue Kinet., 1970, vol. 3, pp. 393-403.

Hudson, et al., Green Fluorescent Protein Bone Marrow Cells Express Hematopoietic and Neural Antigens in Culture and Migrate Within the Neonatal Rat Brain, Journal of Neuroscience Research, 2004, vol. 76, pp. 255-264.

Sanchez-Ramos, et al., Adult Bone Marrow Stromal Cells Differentiate into Neural Cells in Vitro, Experimental Neurology, 2000, vol. 164, pp. 247-256.

Song, et al., Comparison of Neuron-Like Cells Derived from Bone Marrow Stem Cells to Those Differentiated from Adult Brain Neural Stem Cells, Stem Cells and Development, 2007, vol. 16, pp. 747-756.

Brazelton, et al., From Marrow to Brain: Expressions of Neuronal Phenotypes in Adult Mice, Science, 2000, vol. 290, pp. 1775-1779.

Mezey, et al., Turning Blood into Brain: Cells Bearing Neuronal Antigens Generated in Vivo from Bone Marrow, Science, 2000, vol. 290, pp. 1779-1782.

Jin, et al., Induction of Neuronal Markers in Bone Marrow Cells: Differential Effects of Growth Factors and Patterns of Intracellular Expression, Experimental Neurology, 2003, vol. 184, pp. 78-89.

McKay, Stem Cells in the Central Nervous System, Science, 1997, vol. 276, pp. 66-71.

Gage, Mammalian Neural Stem Cells, Science, 2000, vol. 287, pp. 1433-1439.

Arvidsson, et al., Neuronal Replacement from Endogenous Precursors in the Adult Brain After Stroke, Nature Medicine, 2002, vol. 8, No. 9, pp. 963-970.

Kernie, et al., Brain Remodeling Due to Neuronal and Astrocytic Proliferation After Controlled Cortical Injury in Mice, Journal of Neuroscience Research, 2001, vol. 66, pp. 317-326.

Parent, et al., Aberrant Seizure-Induced Neurogenesis in Experimental Temporal Lobe Epilepsy, Annals of Neurology, 2006, vol. 59, No. 1, pp. 81-91.

Ernst, et al., Temporally Specific Proliferation Events are Induced in the Hippocampus Following Acute Focal Injury, Journal of Neuroscience Research, 2006, vol. 83, pp. 349-361.

Suh, et al., Hypoglycemia Induces Transient Neurogenesis and Subsequent Progenitor Cell Loss in the Rat Hippocampus, Diabetes, 2005, vol. 54, pp. 500-509.

Kempermann, et al., Neuroplasticity in Old Age: Sustained Fivefold Induction of Hippocampal Neurogenesis by Long-Term Environmental Enrichment, Annals of Neurology, 2002, vol. 52, No. 2, pp. 135-143.

Van Praag, et al., Running Increases Cell Proliferation and Neurogenesis in the Adult Mouse Dentate Gyrus, Nature Neuroscience, 1999, vol. 2, pp. 266-270.

Kempermann, et al., More Hippocampal Neurons in Adult Mice Living in an Enriched Environment, Nature, 1997, vol. 386, pp. 493-495.

Sanai, et al., Unique Astrocyte Ribbon in Adult Human Brain Contains Neural Stem Cells but Lacks Chain Migration, Nature, 2004, vol. 427, pp. 740-744.

Gould, et al., Neurogenesis in the Neocortex of Adult Primates, Science, 1999, vol. 286, pp. 548-552.

Magavi, et al., Induction of Neurogenesis in the Neocortex of Adult Mice, Nature, 2000, vol. 405, pp. 951-955.

Zhao, et al., Evidence for Neurogenesis in the Adult Mammalian Substantia Nigra, PNAS, 2003, vol. 100, No. 13, pp. 7925-7930.

Frielingsdorf, et al., No Evidence for New Dopaminergic Neurons in the Adult Mammalian *Substantia nigra*, PNAS, 2004, vol. 101, No. 27, pp. 10177-10182.

Jiang, et al., Pluripotency of Mesenchymal Stem Cells Derived from Adult Marrow, Nature, 2002, vol. 418, pp. 41-49.

Castro-Malaspina, et al., Characterization of Human Bone Marrow Fibroblast Colony-Forming Cells (CFU-F) and Their Progeny, Blood, 1980, vol. 56, No. 2, pp. 289-301.

Woodbury, et al., Adult Rat and Human Bone Marrow Stromal Cells Differentiate Into Neurons, Journal of Neuroscience Research, 2000, vol. 61, pp. 364-370.

Beresford, et al., Evidence for an Inverse Relationship Between the Differentiation of Adipocytic and Osteogenic Cells in Rat Marrow Stromal Cell Cultures, Journal of Cell Science, 1992, vol. 102, pp. 341-351.

Prockop, Marrow Stromal Cells as Stem Cells for Nonhematopoietic Tissues, Science, 1997, vol. 276, pp. 71-74.

Weimann, et al., Contribution of Transplanted Bone Marrow Cells to Purkinje Neurons in Human Adult Brains, PNAS, 2003, vol. 100, No. 4, pp. 2088-2093.

Azizi, et al., Engraftment and Migration of Human Bone Marrow Stromal Cells Implanted in the Brains of Albino Rats-Similarities to Astrocyte Grafts, PNAS, 1998, vol. 95, pp. 3908-3913.

Kopen, et al., Marrow Stromal Cells Migrate Throughout Forebrain and Cerebellum, and They Differentiate into Astrocytes After Injection Into Neonatal Mouse Brains, PNAS, 1999, vol. 96, pp. 10711-10716.

Chopp, et al., Spinal Cord Injury in Rat: Treatment with Bone Marrow Stromal Cell Transplantation, NeuroReport, 2000, vol. 11, No. 13, pp. 3001-3005.

Kohyama, et al., Brain from Bone: Efficient "Meta-Differentiation" of Marrow Stromal-Derived Mature Osteoblasts to Neurons with Noggin or a Demethylating Agent, Differentiation, 2001, vol. 68, pp. 235-244.

* cited by examiner

PROMOTION OF BRAIN SELF-REPAIR MECHANISMS BY STEREOTAXIC MICRO-STIMULATION

CROSS REFERENCE TO RELATED APPLICATIONS

This application claims priority under 35 U.S.C. §119(e) to U.S. provisional patent application No. 61/075,586 filed Jun. 25, 2008 which is hereby incorporated by reference into this disclosure.

GOVERNMENT SUPPORT

This invention was made with Government support under Grant No. #DAMD17-03-1-QS01 (2003-06) awarded by the Department of Defense. The Government has certain rights in the invention.

FIELD OF INVENTION

This invention relates to the promotion of brain self-repair mechanisms. Stimulation of specific brain regions through the use of micro-needles induces endogenous stem cells to proliferate, migrate, and promote the brain's self-repair mechanisms. The invention can be applied to but is not limited to augmenting endogenous neurogenesis in order to promote brain repair after injury and neurodegeneration.

BACKGROUND OF THE INVENTION

Stem cells are defined as being self-renewing and multipotent, having the ability to generate into diverse types of differentiated cells. As such, they show promise in the treatment of neurological disorders or trauma. The synaptic connections involved in neural circuits are continuously altered throughout the life of the individual. However, due to synaptic plasticity and cell death, neurogenesis (the generation of new neurons) was thought to be complete early in the postnatal period. The discovery of multipotent neural stem cells (MNSCs) in the adult brain (see, e.g., Alvarez-Buylla et al., 1997. *Neurobiol.* 33: 585-601; Gould et al., 1999, *Science* 286: 548-552) has significantly changed the theory on neurogenesis, given that the presence of MNSCs in the adult brain suggests that regeneration of neurons can occur throughout life.

Over the last few years it has become clear that neurons are generated continuously from adult stem cells in "germinal zones" of the adult brain in rodents (McKay, R., 1997, *Science* 276, 66-71; Gage, F. H., 2000, *Science* 287 (5457), 1433-1439) The adult brain retains a reservoir of neural progenitors in the dentate gyrus (DG) of the hippocampus and the rostral sub-ventricular zone (SVZ) that can proliferate in response to ischemic injury, trauma (Arvidsson, A. et al., 2002, *Nat Med* 8 (9), 963-970; Kernie, S. G. et al., 2001, *J Neurosci Res* 66 (3), 317-326), hypoxia, epilepsy, focal injury (Parent J M. et al., 2006, *Ann Neurology* 59(1), 81-91; Ernst C, Christie B R., 2006, *Journal of Neuroscience Research* 83(3), 349-361; Suh S W. et al., 2005, *Diabetes* 54(2), 500-509) and to other stimuli such as exercise or provision of an enriched environment (Kempermann, G. et al., 1997, *Nature* 386 (6624), 493-495; van Praag, H. et al., 1999, *Nat Neurosci* 2 (3), 266-270; Kempermann, G. et al., 2002, *Ann Neurol* 52 (2), 135-143). The entire ventricular wall of the human brain has been shown to be lined with a "ribbon" of neural progenitors capable of generating neurons in vitro, but the fate of these progenitors in vivo appears limited to glial lineages (Sanai, N. et al., 2004, *Nature* 427 (6976), 740-744). Other regions of the brain such as the cerebral cortex and the midbrain have been reported to have potential for neurogenesis, though these findings remain controversial (Gould, E. et al., 1999, *Science* 286 (5439), 548-552; Magavi, S. S. et al., 2000, *Nature* 405 (6789), 951-955; Zhao, M. et al., 2003, *PNAS* 100 (13), 7925-7930; Frielingsdorf, H. et al., 2004, *PNAS* 101 (27), 10177-10182).

Bone marrow is well known to house stem cells that regenerate all the blood lineages throughout life. A growing focus of research has been on the discovery of more "primitive" multipotent stem cells in bone marrow that are capable of giving rise to tissues of all embryonic germ layers (Jiang, Y. et al., 2002, *Nature* 418 (6893), 41-49). Bone marrow contains at least two types of stem cells, hematopoietic stem cells and stem cells of non-hematopoietic tissues variously referred to as mesenchymal stem cells or marrow stromal cells (MSCs) or bone marrow stromal cells (BMSCs). BMSCs are easily isolated from a small aspirate of bone marrow and they readily generate single-cell derived colonies. The single-cell derived colonies can be expanded through as many as 50 population doublings in about 10 weeks, and can differentiate into osteoblasts, adipocytes, chondrocytes (Friedenstein et al., 1970, *Cell Tissue Kinet.* 3: 393-403; Castro-Malaspina et al., 1980, *Blood* 56: 289-301; Beresford et al., 1992, *J. Cell Sci.* 102: 341-351; Prockop, 1997, *Science* 276: 71-74), myocytes (Wakitani et al., 1995, *Muscle Nerve* 18: 1417-1426), astrocytes, oligodendrocytes, and neurons (Azizi et al., 1998, *Proc. Natl. Acad. Sci. USA* 95: 3908-3913); Kopen et al., 1999, *Proc. Natl. Acad. Sci. USA* 96: 10711-10716; Chopp et al., 2000, *Neuroreport II* 3001-3005; Woodbury et al., 2000, *Neuroscience Res.* 61: 364-370).

Adult bone marrow retains a reservoir of multi-potent stem cells and BMSCs can be used as an alternative source of multi-potent stem cells. Bone marrow-derived cells have been shown by independent investigators to give rise to neural cells and these may migrate to brain where they appear to differentiate into neurons and glia (Sanchez-Ramos, J. et al., 2000, *Experimental Neurology* 164, 247-256; Woodbury, D. et al., 2000, *Journal of Neuroscience Research* 61 (4), 364-370; Mezey, E. et al., 2000, *Science* 290 (5497), 1779-1782; Brazelton, T. R. et al., 2000, *Science* 290 (5497), 1775-1779). The mechanism for transdifferentiation of bone marrow to neural cells is not clear and may reflect the capacity of bone marrow derived cells to fuse with injured neurons (Weimann, J. M. et al., 2003, *Proc Natl Acad Sci USA* 100 (4), 2088-2093). Fusion mechanism aside, there are many experiments in vitro that demonstrate subpopulations of bone marrow cells (and single derived clones) can be induced to differentiate into neural phenotypes (Sanchez-Ramos, J et al., 2000, *Experimental Neurology*, 164:247-256; Woodbury D, et al., 2000, *Journal of Neuroscience Research* 61 (4), 364-370; Kohyama J, et al., 2001, *Differentiation* 68:235-244; Jiang Y, et al., 2002, *Nature* 418:41-49; Jin K, et al., 2003, *Experimental Neurology* 184:78-89).

U.S. Patent Application 2005/0169896A1 to Li et al. provides further evidence to establish that BMSCs can differentiate into neurons and these cells can have added therapeutic benefit in CNS injuries and diseases when transplanted into a patient suffering from a neurodegenerative disease or neural injury. It was found that transplanted bone marrow cells activated the endogenous stem cells and ependymal cells in the brain to proliferate and differentiate into parenchymal cells including neurons. These bone marrow cells were found to have produced an array of factors, including cytokines and growth factors that promote repair and plasticity of the brain.

Additional evidence of BMSCs differentiating into neurons was substantiated by this laboratory. We found that both nestin-enriched cells derived from bone marrow and adult brain neural stem cells can differentiate into cells with the morphological, immunocytochemical, and functional characteristics of neurons (Song S, et al., 2007, *Stem Cells and Development* 16:747-756).

It has been well established that both brain and bone marrow retain an endogenous population of stem cells that proliferate in response to environmental and pharmacological manipulations. These stem cells can replace those cells lost in some experimental lesions. However, neurodegenerative disorders such as Alzheimer's, Parkinson's, and Huntington's diseases are characterized by continuous loss of neurons. The prevalence of these human neurodegenerative diseases underscores the inadequacy of self-repair through neurogenesis.

Many neurological deficits are localized to particular brain regions. A "neurological deficit" is a condition caused by a wide variety of diseases and injuries, including age, trauma, malfunction, and degeneration, that causes loss of brain and/or nervous system function. Neuronal degeneration in specific brain locations can lead to the inability of the brain to synthesize and release neurotransmitters that are necessary to neural signaling.

Alzheimer's disease is due to a degenerative process that is characterized by the progressive loss of cells from the basal forebrain, cerebral cortex, hippocampus, and other brain areas. Acetylcholine-transmitting neurons and their target nerves are particularly affected. Alzheimer's disease results in impaired memory, thinking, and behavior. Alzheimer's disease is characterized by a buildup of amyloid beta protein, which produces neuritic plaques between the neurons, and tau protein neurofibrillary tangles in which the protein strands twist around each other and damage local neurons.

Parkinson's disease is another progressive neurodegenerative disease. The brain areas with the most regularly observed changes have been in the aggregates of melanin-containing nerve cells in the brainstem (substantia nigra, locus coeruleus). Parkinson's disease affects the central nervous system and is often characterized by tremors, stiffness of joints, difficulty in movement, and speech difficulties.

Huntington's disease is another neurodegenerative disease which affects the central nervous system and is characterized by unsteady gait, abnormal posturing, rigidity, and impaired psychomotor functions. Huntington's disease affects the striatum and the substantia nigra, as well as other areas of the brain including the cerebral cortex, cerebellum, and hippocampus.

The inability of neurogenesis by endogenous neural stem cells or neuronal rescue by bone marrow derived cells to keep pace with neurodegeneration has underscored the need for a method to induce endogenous stem cells to proliferate, migrate, and differentiate in order to promote the self-repair mechanisms of the brain. We have discovered that micro-stimulation of a brain region by transient insertion and removal of a fine needle will stimulate the self-repair mechanisms of the brain.

SUMMARY OF INVENTION

An illustrative embodiment of the present invention includes a method of stimulating the repair mechanisms of the brain. In the first step, the coordinates of the region to be stimulated are established. This procedure is preferably performed through the use of computed tomographic (CT) scanning.

The brain regions to be stimulated can be any region that is affected by neurological deficit. Preferably the brain regions to be stimulated are the hippocampus, ventral midbrain, cerebellum, and corpus striatum.

Entry to the skull is then obtained by drilling a hole in the skull. This hole is preferably a trephine hole.

A micro-needle is then gently and transiently inserted into the area of the brain affected by the neurological deficit. The micro-needle is preferably inserted through the use of a stereotaxic guide. The micro-needle preferably has a shaft diameter that is less than about 200 microns.

The micro-needle is then gently removed. The transient insertion and subsequent removal of the needle causes a birth of new neural cells within the brain itself as well as the arrival of cells from outside the brain to the site of stimulation. The cells that are born within the brain are derived from "neurogenic zones" of the brain. Other cells come into the brain from the bloodstream, originating from the bone marrow. The precise, focal stimulation by the micro-needle causes a cascade of signals that mobilizes cells from the bone marrow to the blood stream from which they migrate into the point of injury in the brain.

In another embodiment, there is presented a method of treating neural deficit through inducing the endogenous stem cells to proliferate, migrate and promote the brain's self-repair mechanisms by stimulation of brain areas with a micro-needle. Preferably, the brain area to be stimulated is the hippocampus, ventral midbrain, cerebellum, and corpus striatum. The stem cells can be multipotent neural stem cells and/or bone marrow derived stem cells.

In another embodiment, there is presented a method of treating neural deficit through stimulating neural stem cells and bone marrow derived stem cells to promote the brain's repair mechanisms. Preferably the bone marrow is endogenous to the patient however bone marrow may also be obtained through a bone marrow transplant that is performed at a sufficient time prior to stereotaxic surgery.

BRIEF DESCRIPTION OF THE DRAWINGS

For a fuller understanding of the invention, reference should be made to the following detailed description, taken in connection with the accompanying drawings, in which:

FIG. 2A is an image in which GFP and TH are depicted in brain tissue of euthanized mice that had undergone micro-needle stimulation. The presence of GFP+ indicates bone marrow derived cells in the *s. nigra*. The presence of TH indicates tyrosine hydroxylase immunoreactive (TH+) neurons in the *s. nigra*. No cells were found that expressed both TH and GFP.

FIG. 2B is an image of brain tissue of mice that had undergone micro-needle stimulation depicting that GFP+ bone marrow-derived cells infiltrated the lesion site in the dorsal striatum.

FIG. 2C1 is an image of brain tissue of mice that had undergone micro-needle stimulation depicting GFP+ cells in the dorsal striatum.

FIG. 2C2 is an image of brain tissue of mice that had undergone micro-needle stimulation depicting cells expressing the CD11b signal, a marker of microglia in the dorsal striatum.

FIG. 2C3 is an image of brain tissue of mice that had undergone micro-needle stimulation depicting cells expressing merged signals of GFP and CD11b in the dorsal striatum. Yellow cells co-express GFP and CD11b, indicating an origin from the peripheral circulation.

FIG. 2D is an image of brain tissue of mice that had undergone micro-needle stimulation depicting cells expressing doublecortin (DCX), a marker of young migrating neurons, in the dorsal striatum. Cells that expressed both DCX and GFP were rare in the dorsal striatum FIG. 2E is an image depicting cells expressing BrdU in the s. nigra. BrdU indicates the presence of a cell that was born at the time of micro lesion placement (2 weeks earlier). The arrow indicates a TH+ neuron that co-expresses BrdU.

FIG. 2F1 is an image depicting GFP+ cells derived from the peripheral circulation that infiltrated the dentate gyrus of the hippocampus following a micro lesion to the dorsal hippocampus.

FIG. 2F2 is an image depicting GFP+ cells derived from the peripheral circulation that infiltrated the dentate gyrus of the hippocampus following a micro lesion to the dorsal hippocampus in which the cells also co-expressed doublecortin (DCX), a marker of young migrating neurons.

FIG. 3 is a series of photographs depicting the immunochemistry of a brain slice one week after stereotaxic micro-stimulation.

FIG. 3A is an image depicting cells in the hippocampus taken one week after stereotaxic micro-stimulation. The cells are expressing NeuN in the first image; BrdU in the second image; and NeuN and BrdU merged in the third image.

FIG. 3B is an image depicting cells in the hippocampus taken one week after stereotaxic micro-stimulation. The cells are expressing Tuj1 in the first image; BrdU in the second image; and Tuj1 and BrdU merged in the third image.

FIG. 3C is an image depicting cells in the hippocampus taken one week after stereotaxic micro-stimulation. The cells are expressing DCX in the first image; BrdU in the second image; and DCX and BrdU merged in the third image.

FIG. 3D is an image depicting cells in the hippocampus taken one week after stereotaxic micro-stimulation. The cells are expressing MAP2 in the first image; BrdU in the second image; and MAP2 and BrdU merged in the third image.

FIG. 3E is an image depicting cells in the hippocampus taken one week after stereotaxic micro-stimulation. The cells are expressing GFAP in the first image; BrdU in the second image; and GFAP and BrdU merged in the third image.

FIG. 4A is an image depicting Pukinjin cells in the cerebellum taken four weeks after stereotaxic micro-stimulation. The cells are expressing calbindin in the first image; BrdU in the second image; and calbindin and BrdU merged in the third image.

FIG. 4B is an image depicting striatal cells taken two weeks after stereotaxic micro-stimulation. The cells are expressing nestin in the first image; BrdU in the second image; and nestin and BrdU merged in the third image.

FIG. 4C is an image depicting cortex cells taken one week after stereotaxic micro stimulation. The cells are expressing nestin in the first image; BrdU in the second image; and nestin and BrdU merged in the third image.

FIG. 4D is an image depicting cortex boule cells from a chimeric GFP bone marrow mouse taken one week after stereotaxic micro-stimulation. The cells are expressing GFP in the first image; calbindin in the second image; and GFP and calbindin merged in the third image.

FIG. 4E is an image depicting striatal cells from a chimeric GFP bone marrow mouse taken one week after stereotaxic micro-stimulation. The cells are expressing GFP in the first image; Tuj1 in the second image; and GFP and Tuj1 merged in the third image.

DETAILED DESCRIPTION OF THE PREFERRED EMBODIMENT

Figure 1:
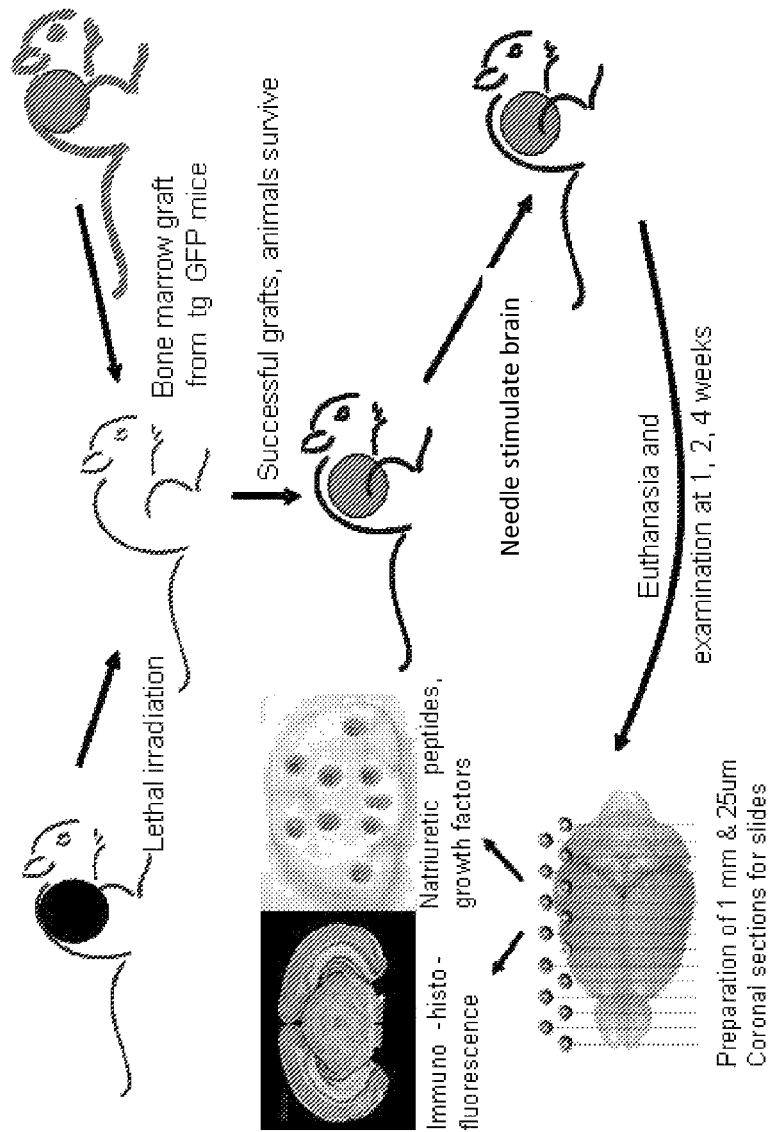
FIG. 1 is a process flow diagram depicting the experimental process for promoting self-repair mechanisms in the brain

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Acupuncture is a kind of traditional Chinese Medicine has been used to treat diseases, relieve pain, and spasm for thousands of years. However, this approach has not had an impact on progressive neurodegenerative diseases such as Alzheimer's disease, Parkinson's disease, and Huntington's disease because in traditional acupuncture, the needle is never inserted into central nervous system (CNS).

Our laboratory has found that focal and precise stimulation of specific brain regions with an acupuncture needle (micro-needle) induces endogenous stem cells to proliferate, migrate and promote the brain's self-repair mechanisms. A micro-needle is defined as a small needle, similar to an acupuncture needle, in which the shaft diameter is less than 200 microns. In the present study, mice were irradiated and subsequently given a bone marrow transplant wherein the cells were allowed to reconstitute for two months prior to micro-needle stimulation. The mice were anesthetized and mounted onto a device that allows focal and precise insertion of an acupuncture needle into specific regions of the brain. This procedure, known as stereotaxic surgery, is routinely used in human brain surgery for placement of electrodes or to make lesions to alleviate tremor and rigidity in Parkinson's disease.

The stereotaxic micro-stimulation inducing neurogenesis in the adult mouse brain suggests that endogenous stem cells/precursors are a potential source for neuronal replacement after injury and neurodegeneration. The micro-stimulation results in the birth of new neural cells within the brain itself as well as the arrival of cells from outside the brain to the site of stimulation. The cells that are born within the brain are derived from "neurogenic zones" of the brain. These "neurogenic zones" include, but are not limited to, the dentate gyrus (DG) of the hippocampus, the rostral sub-ventricular zone (SVZ), the ventricular wall, the cerebral cortex and the midbrain.

Other cells come into the brain from the bloodstream, originating from the bone marrow. Insertion of the needle into the brain triggers a cascade of signals, including but not limited to growth factors, trophic factors, and cytokines and augments these signals that mobilize cells from the bone marrow to the bloodstream and into the brain. Some of the bone marrow-derived cells are involved in mediating the immune response to the micro-injury and some are actually precursors to neurons that eventually differentiate into neurons and other neural cells (astrocytes) to replace the degenerative cells and repair the diseased brain tissue. By repairing and/or replacing injured or dead cells, this approach will slow down the degenerative course of the disease and may result in reversal of symptoms.

A recent study indicates that 1-methyl-4-phenyl-1,2,3,6-tetrahydropyridine (MPTP) doubles the number of BM-derived cells that penetrate the brain. Most of the BM-derived cells from the peripheral circulation were microglial and were believed to contribute to the nigral lesion. In contrast, in our work, we used a very thin needle (shaft diameter less than 200 microns) to stimulate hippocampus, striatum, substantial nigra and cerebellum. At the time of micro-stimulation, animals were injected with BrdU to label proliferating cells (to mark the "birthday" of the cell). After one, two, and four weeks, we observed many bromodeoxyuridine (BrdU) positive cells at the site of stimulation. After two weeks some BrdU+ cells co-expressed neuronal markers indicating that the newly born cell had differentiated into a young neuron.

The present invention provides a method for stimulating the repair mechanisms in the brain. In a preferred embodiment, the stimulation of the brain's repair response and augmentation of endogenous neurogenesis is accomplished by transient insertion of a fine acupuncture needle into precise regions of the brain. Preferably, the shaft diameter of the micro-needle is no larger than 200 microns. Stereotaxic surgery is preferably used to introduce the micro-needle into the brain.

The stimulation is preferably administered to a mammal suffering from a disease, disorder, or condition involving the CNS and resulting in a neurological deficit. The precise site of stimulation depends on any number of factors, including but not limited to, the brain site affected by the neurological deficit, the type of disease being treated, the age of the human and the severity of the disease and the like. Determination of the site of stimulation is well within the skill of the artisan versed in the stimulation of brain areas. The preferred areas to be stimulated include, but are not limited to, the hippocampus, ventral midbrain, cerebellum, and corpus striatum.

In this preferred embodiment, the coordinates of the brain region to be stimulated can be established through the use of methods well known in the art including, but not limited to, computed tomographic (CT) scanning and magnetic resonance imaging (MRI). The bregma can be used as a reference point and a trephine hole can be drilled into the skull to gain direct access to the brain.

The invention also provides a method of treating neurological deficits. In one embodiment, the coordinates of the brain area to be stimulated are preferably established through CT scanning after which a hole is drilled into the skull to gain direct access to the brain. The stem cells are then stimulated through the transient and gentle insertion and removal of the micro-needle. The stimulation by the micro-needle induces the endogenous stem cells to proliferate, migrate and promote the brain's self-repair mechanisms. The stem cells can be any endogenous stem cells including, but not limited to, multipotent neural stem cells and bone marrow derived stem cells. The bone marrow stem cells can be endogenous to the subject or can be obtained through a bone marrow transplant performed prior to micro-needle stimulation. If a bone marrow transplant is performed, it is preferable to allow a sufficient amount of time to elapse before micro-stimulation in order to allow the cells to reconstitute. The bone marrow derived cells can migrate to the brain region to be stimulated and can differentiate into neural cells.

The approach of the present invention can be used to slow down progression or reverse the symptoms of neurodegenerative diseases especially for Alzheimer's, Parkinson's, and Huntington's diseases as well as many others. Therefore, using acupuncture to augment endogenous neurogenesis in the adult can offer useful therapies for brain repair after injury and neurodegeneration.

Materials and Methods

Preparation of Bone Marrow Cells:

In accordance with protocols by Sanchez-Ramos and co-workers (Sanchez-Ramos et al., 2000, *Experimental Neurology* 164:247-256; Song, S, and Sanchez-Ramos, J., 2002, *Methods in Molecular Biology* 198:79-88), incorporated herein by reference, bone marrow cells were collected from adult male GFP transgenic mice (3-6 month old) femur and tibias by flushing the shaft with buffer (phosphate buffered saline (PBS, Invitrogen)) supplemented with 0.5% bovine serum albumin (BSA, Sigma, pH 7.2)) using a syringe with a #20-23 G needle. Cells are disaggregated by gentle pipetting several times. Cells were passed through 40 μm nylon cell strainer to remove remaining clumps of tissue. Cells were washed by adding buffer, centrifuged for 10 minutes at 200×g and the supernatant was discarded. The cell pellet was re-suspended in saline, with 8-10 million cells/mouse by tail vein.

Creation of a chimeric mouse with GFP+ bone marrow that generates GFP+ stem/progenitor cells and GFP+ circulating mononuclear cells:

Three month old male C57BL/6J mice were lethally irradiated with 8 Gy total body irradiation (delivered in two fractions of 4 Gy at dose rate of 1.03 Gy/min in a Gammacell 40 Extractor, followed by rescue with a bone marrow transplant ($8\times10^6$ mononuclear cells) from tg GFP mice (all cells constitutively express GFP) of the same genetic background. (FIG. 1.)

Stereotaxic Surgery:

After accepting irradiation and GFP bone marrow transplantation two month later, the adult male mice were anesthetized with sodium pentobarbital (50 mg/kg, i.p.) before being placed in a stereotaxic frame. Using the bregma as the reference point, a trephine hole was then drilled on skull, and a sterile micro-needle (max shaft diameter of 200 microns) was gently inserted into hippocampus (AP-2.5 mm; ML 1.3 mm; DV 3.5 mm), *s. nigra* (AP-3.5 mm; ML 1.3 mm; DV 4.5 mm), cerebellum (AP-7 mm; ML 1.8 mm; DV 3.0 mm), and striatum (AP-0.58 mm; ML 1 mm; DV 2.6 mm). The mice underwent bromodeoxyuridine (BrdU) injections (100 mg/kg i.p.×2) on the day of transient insertion of the needle to label newly born cells. All the animal experiments are conducted under the approval of the USF's and James A. Haley VA Hospital's Animal Use and Care Committee.

Tissue Preparation and Sectioning Techniques:

One, two, and four weeks after micro-needle stimulation the mice were anesthetized under deep chloral hydrate (10%) anesthesia. A transcardial perfusion of the brain with 20 ml saline (0.9% NaCl) and then 50 ml 4% paraformaldehyde in 0.1 M PBS was followed by removal of the brain and 48 hours post-fixation in the same solution. The brains were immersed overnight in 20% sucrose in PBS and 30 μm thick frozen sections through the striatum were collected and stored in vials containing a cryopreservation solution.

Immunohistochemistry:

Tissue sections were pre-incubated 10% normal serum (goat or donkey; Vector) in 0.3% triton X-100 (Sigma) in PBS for 30 min. The sections were then transferred to primary antibodies in 1% normal serum, 0.3% triton X-100/PBS and incubated overnight at 4° C. The specific antibodies used in each experiment were the following: thymidine analog BrdU, a marker of DNA synthesis, rat anti-BrdU (monoclonal antibody, Serotec) 1:100 in PBS containing 1:100 normal serum and 0.3% Triton X-100; mouse anti-neuronal nuclei (NeuN, monoclonal antibody, Chemicon) 1:50 in PBS containing 1:100 normal serum and 0.3% Triton X-100; mouse anti-Nestin (monoclonal, BD Biosciences) 1:50 same as above; goat anti-Doublecortin (DCX, polyclonal, Santa Cruz Biotechnology) 1:50 same as above; mouse anti-β-Tubulin III (Tuj1, monoclonal, Sigma) 1:400; Rabbit anti-Microtubule-associated protein 2 (MAP2, polyclonal, Chemicon) 1:500; rabbit anti-Calbindin (polyclonal, Chemicon) 1:200; rabbit anti-Tyrosine Hydroxylase (TH, polyclonal, Chemicon) 1:500; rat anti-mouse CD11b (monoclonal, Chemicon) 1:20; rabbit anti-Amyloid Precursor Protein (polyclonal, abcm Inc) 1:200; rat anti-CD45 (monoclonal, Chemicon) 20 μg/ml; rabbit anti-Glial Fibrillary Acidic Protein (GFAP, polyclonal, BioGenex) 1:50 in PBS containing 1:100 normal serum without Triton X-100. After being washed, the cells were incubated for 1 hour with Alexa Fluor Goat anti-mouse IgG or Goat anti-rabbit IgG (Molecular Probes) at room temperature; Alexa Fluor 488 diluted 1:500 in PBS; and Alexa Fluor 546 diluted 1:1000 in PBS. The sections were then rinsed in PBS three times and covered with a cover slip. Some slides were stained with DAP (300 nM) for counterstaining. DAPI staining was normally performed after all other staining. Fluorescent signals from the labeled cells were visualized with fluorescence microscopy using appropriate filters or with Zeiss LSM 510 confocal fluorescence microscope.

Creation of a chimerical mouse with GFP+ bone marrow that generates GFP+ stem/progenitor cells and GFP+ circulating mononuclear cells:

C57BL/6J mice were lethally irradiated with 8 Gy total body irradiation (delivered in two fractions of 4 Gy at dose rate of 1.03 Gy/min in a Gammacell 40 Extractor, followed by rescue with a bone marrow transplant ($8 \times 10^6$ mononuclear cells) from tg GFP mice (all cells constitutively express GFP) of the same genetic background. Eight of 12 mice survived and exhibited GFP+ mononuclear cells in their peripheral blood. At 2 months after rescue with GFP+ bone marrow, the mice underwent stereotaxic surgery to produce focal micro lesions in the *s. nigra* as well as the striatum, hippocampus and cerebellum (FIG. 1). This preliminary experiment was done in order to assess the extent of mobilization of GFP+ bone marrow cells to the site of the lesion before undergoing the disease model mice.

EXAMPLE

Figure 2:
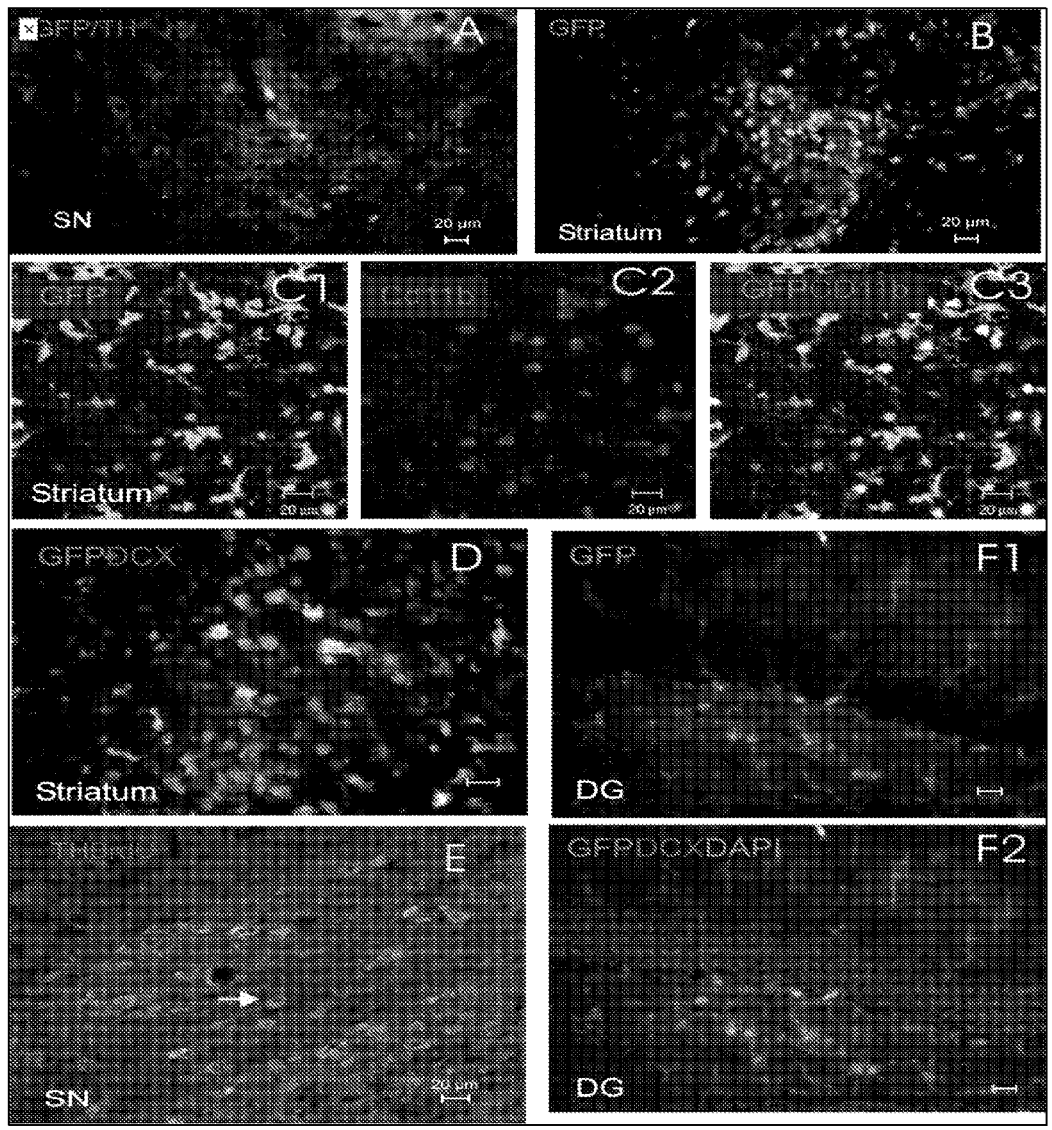
FIG. 2 is a series of photographs of brain tissues. A sterile acupuncture needle (200 microns maximum shaft diameter, similar to the acupuncture needle) was transiently inserted stereotaxically into three different sites (v. midbrain, striatum and hippocampus) in chimerical mice which had undergone whole-body irradiation 2 months earlier followed by rescue with GFP+ bone marrow. Several of the mice underwent BrdU injections (100 mg/kg i.p.×2) on the day of transient insertion of the micro-needle to label newly born cells. Animals were euthanatized 2 weeks after placement of the focal micro lesions.

Mobilization of GFP+ Cells from the Periphery in to the CNS Following Focal Micro-Lesions of Brain A sterile micro-needle (200 microns maximum shaft diameter, similar to the acupuncture needle) was transiently inserted stereotaxically into four different sites: corpus striatum, dorsal hippocampus, cerebellum and ventral midbrain. Several of the mice underwent bromodeoxyuridine (BrdU) injections (100 mg/kg i.p.×2) on the day of transient insertion of the needle to label newly born cells. One, two and four weeks after making the micro-lesions, mice were euthanatized and their brains were processed for immunohistochemistry. GFP+ cells were readily visualized at the site of the micro-lesions in striatum, ventral midbrain and hippocampus (FIG. 2). The GFP+ cells could be found along the tract of the needle and extending beyond the locus of the lesion. In the striatal lesion (FIG. 2B, 2C) many of the GFP+ cells that had infiltrated the lesion from the peripheral circulation bore the microglial marker CD11b. Some GFP+ cells in the striatum expressed markers of young migrating neurons including doublecortin (DCX) and β III tubulin (Tuj1) (FIGS. 2D, 3B and C, 4E).

Figure 3:
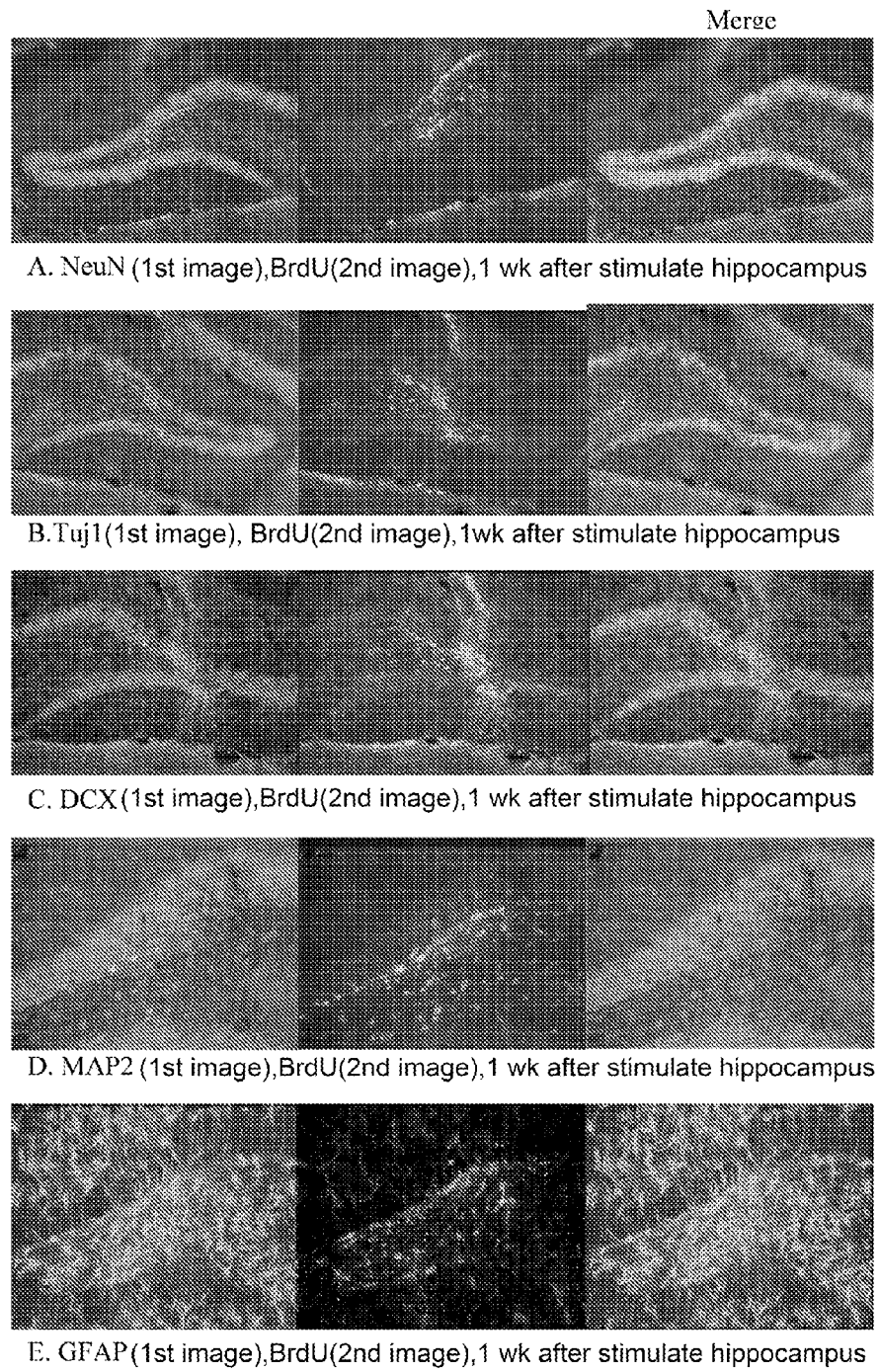
Figure 4:
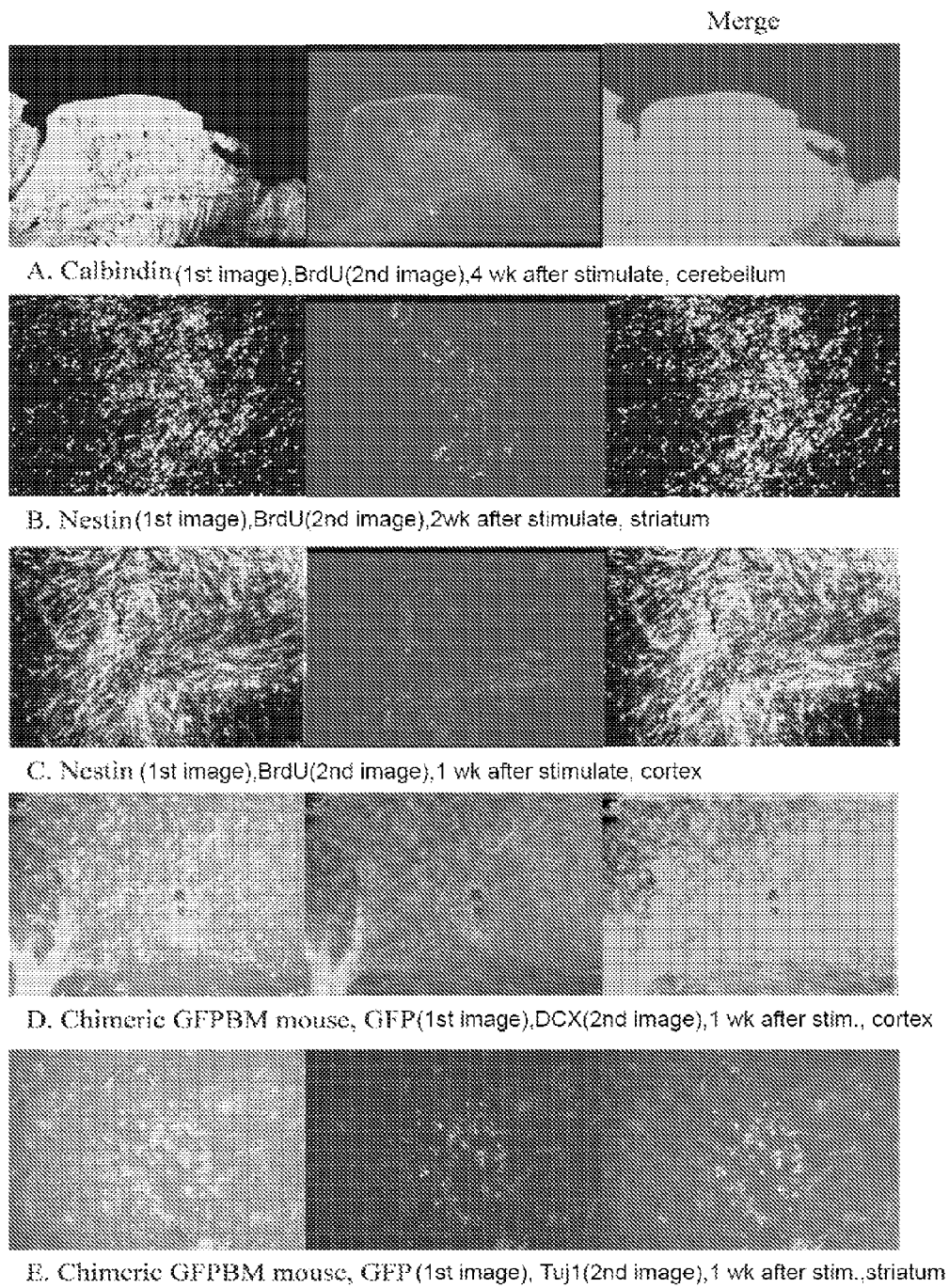
FIG. 4 is a series of photographs depicting the immunochemistry of slices from various regions of the brain taken at various timepoints after stereotaxic micro-stimulation.

In the ventral midbrain lesion, GFP+ cells could be found along the needle track ending in a small lesion of the *s. nigra* (FIG. 2A). Rare co-labeling of tyrosine hydroxylase (TH) positive cells with BrdU was found (FIG. 2E), suggesting that TH+ cells either underwent successful DNA repair or had differentiated from neural progenitors derived from bone marrow. However, TH+/GFP+ cells were not found, indicating that transdifferentiation of bone marrow cells to neurons had not occurred at that site. In the hippocampal lesion, GFP+ cells, as well as BrdU+ cells were abundant in the sub-granular zone of the dentate gyrus (the site of neurogenesis). Co-labeling revealed some doublecortin-expressing cells (DCX+), a marker of migrating young neurons; Tuj1-expressing cells, a young neuron marker; Neuron-Specific Nuclear Protein (NeuN) and Microtubule-Associated Protein (MAP2), markers expressed by mature neurons (FIGS. 3 and 4). Some of the cells expressed microglial markers (CD11b).

Figure 5:
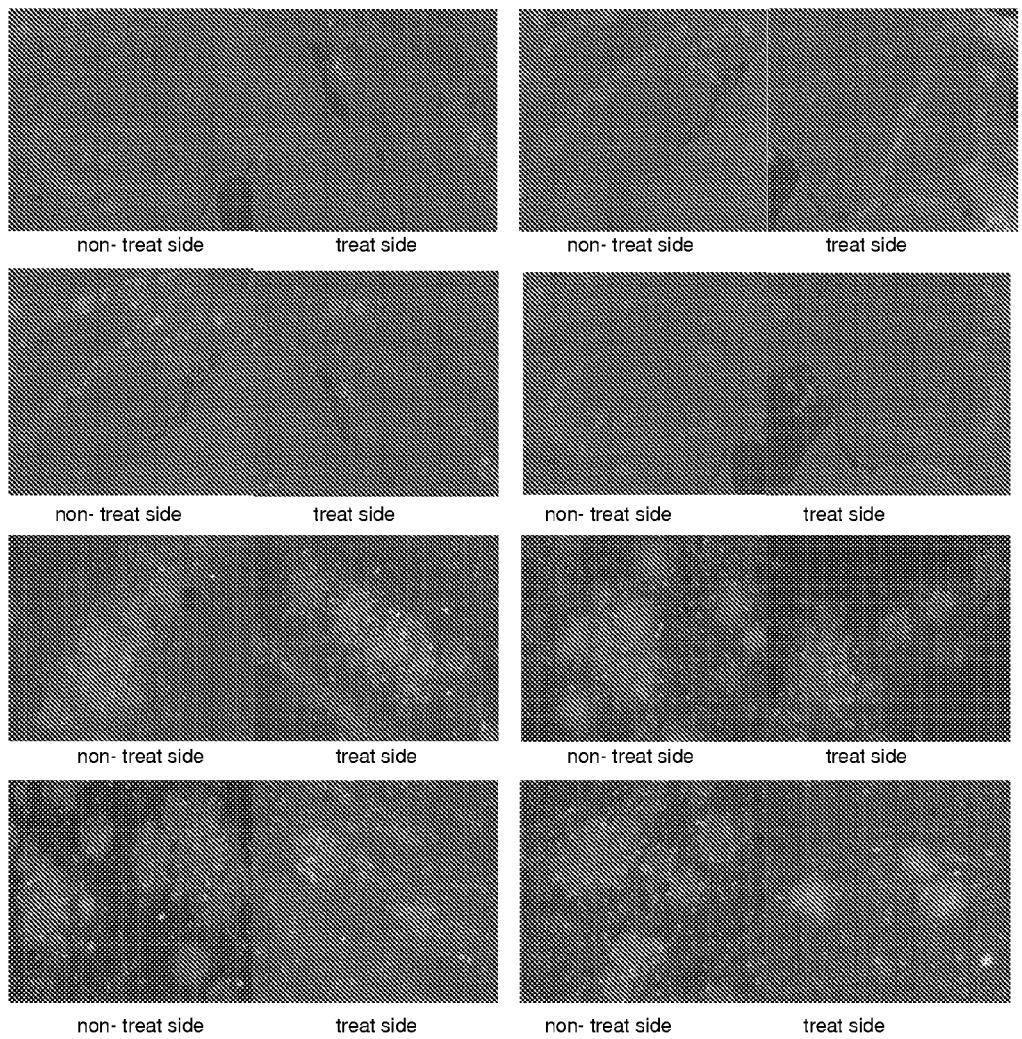
FIG. 5 is a series of images depicting beta amyloid plaque decrease and micro-glial cells increase (treated side) one week after stereotaxic micro-stimulation in APP (amyloid precursor protein) transgenic mice brains.
Figure 6:
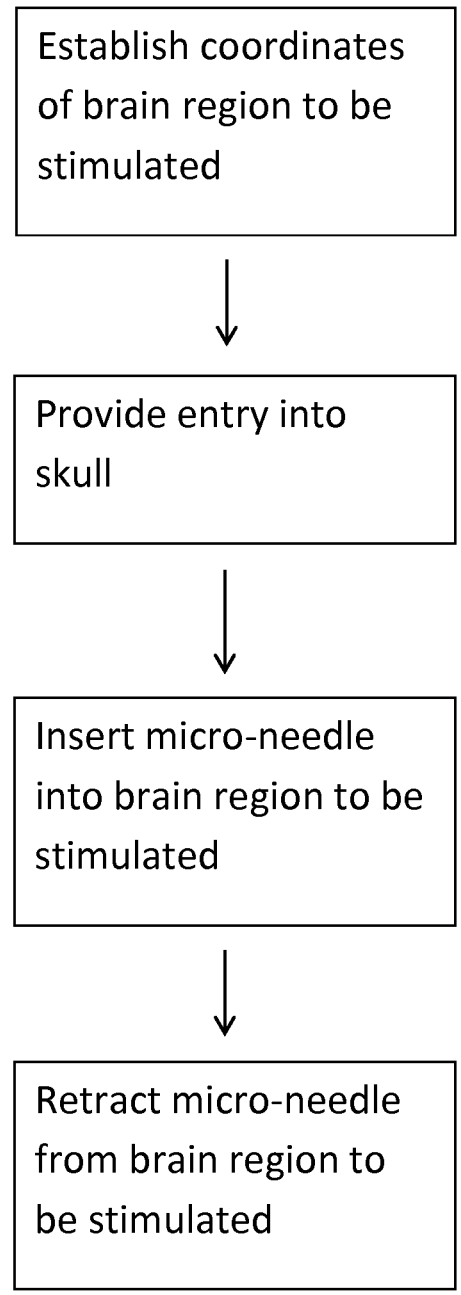
FIG. 6 is a flow chart depicting the recited steps of the invention.

We also examined the effect micro-needle stimulation would have on beta amyloid plaques and micro-glial cells. We observed that one week after stereotaxic micro-stimulation, beta amyloid plaque decreased and micro-glial cells increased in the treated side as compared to the non-treated side. (FIG. 5). This observation supports our findings that stereotaxic micro-needle stimulation promotes the brain's self-repair mechanisms and causes the stem cells to proliferate, migrate, and differentiate into neural cells.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

While there has been described an illustrated specific embodiments of a method of inducing the self-repair mechanisms of the brain, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:
1. A method of inducing neurogenesis in a brain comprising the steps of:
   establishing coordinates of a brain region to be manually stimulated;
   providing entry into a skull;

manually stimulating the brain region by inserting a non-electrode acupuncture micro-needle into the brain region to be manually stimulated; and retracting the acupuncture micro-needle from the brain region wherein the insertion and retraction of the micro-needle induces neurogenesis.

2. The method of claim 1 wherein the coordinates of the brain region to be stimulated are established by computed tomographic (CT) scanning.

3. The method of claim 1 wherein the brain region to be stimulated is selected from the group consisting of hippocampus, ventral midbrain, cerebellum, and corpus striatum.

4. The method of claim 1 wherein entry into the skull is performed by drilling a hole in the skull.

5. The method of claim 4 wherein the hole is trephine.

6. The method of claim 1 wherein introducing the acupuncture micro-needle into the brain region to be stimulated is performed by stereotaxic surgery.

7. The method of claim 1 wherein the micro-needle has a shaft diameter of less than about 200 microns.

8. A method of treating neurological deficit comprising the steps of:

establishing coordinates of a brain region to be manually stimulated;

drilling a hole in a skull for direct access to the brain;

manually stimulating the brain region by inserting a non-electrode acupuncture micro-needle stereotaxically into the brain region to be stimulated; and retracting the acupuncture micro-needle from the brain region wherein the insertion and retraction of the acupuncture micro-needle stimulates stem cells to induce neurogenesis wherein the induced neurogenesis treats the neurological deficit.

9. The method of claim 8 wherein the coordinates of the brain region to be stimulated are established by CT scanning.

10. The method of claim 8 wherein the brain region to be stimulated is selected from the group consisting of hippocampus, ventral midbrain, cerebellum, and corpus striatum.

11. The method of claim 8 wherein the hole drilled in the skull is trephine.

12. The method of claim 8 wherein the stem cells are bone marrow derived stem cells, previously introduced by a bone marrow transplant, that migrate to the brain in response to signals induced by the insertion and retraction of the acupuncture micro-needle.

13. The method of claim 8 wherein the micro-needle has a shaft diameter less than about 200 microns.

14. A method of decreasing beta amyloid plaques in the brain comprising the steps of:

establishing coordinates of a brain region to be manually stimulated through the use of CT scanning;

drilling a trephine hole in a skull for direct access to the brain; and stimulating stem cells further comprising the steps of:

inducing neurogenesis by inserting a non-electrode acupuncture micro-needle stereotaxically into the brain region to be stimulated; and retracting the acupuncture micro-needle from the brain region wherein the insertion and retraction of the acupuncture micro-needle acts to decrease the beta amyloid plaques in the brain.

15. The method of claim 14 wherein the brain region to be stimulated is selected from the group consisting of hippocampus, ventral midbrain, cerebellum, and corpus striatum.

16. The method of claim 14 wherein the stem cells are endogenous stem cells.

17. The method of claim 14 wherein the stimulated stem cells are derived from bone marrow obtained from a previous bone marrow transplant occurring prior to any brain injury wherein the stem cells migrate to the brain region stimulated in response to signals induced by the insertion and retraction of the micro-needle.

18. The method of claim 14 wherein the micro-needle has a shaft diameter of less than about 200 microns.

* * * * *